(12) United States Patent
Blackford

(10) Patent No.: US 8,286,638 B1
(45) Date of Patent: Oct. 16, 2012

(54) FOOT STABILIZING DEVICE

(76) Inventor: Robert E. Blackford, Medford, OR (US)

( * ) Notice: Subject to any disclaimer, the term of this patent is extended or adjusted under 35 U.S.C. 154(b) by 0 days.

(21) Appl. No.: 12/856,248

(22) Filed: Aug. 13, 2010

(51) Int. Cl.
*A61F 5/37* (2006.01)

(52) U.S. Cl. ........................... 128/882; 5/651

(58) Field of Classification Search .......... 128/882; 5/651; 223/111–113, 118
See application file for complete search history.

(56) References Cited

U.S. PATENT DOCUMENTS

| | | | |
|---|---|---|---|
| 2,676,597 A | 4/1954 | Colbert | |
| 2,891,257 A | 6/1959 | Posey | |
| 3,033,309 A * | 5/1962 | Fugere | 182/90 |
| 3,770,316 A | 11/1973 | Barkhuff | |
| 4,222,136 A | 9/1980 | Valentino | |
| 4,489,448 A | 12/1984 | Cairo | |
| 4,524,475 A | 6/1985 | Valentino | |
| 5,340,070 A | 8/1994 | Soma | |
| 5,465,435 A | 11/1995 | Malvaez et al. | |
| 5,642,541 A | 7/1997 | Corbin | |
| D388,289 S * | 12/1997 | Denison et al. | D7/692 |
| 5,774,913 A | 7/1998 | Allen et al. | |
| 5,894,970 A * | 4/1999 | Belkin et al. | 223/112 |
| 6,056,171 A | 5/2000 | Santamaria | |
| 6,101,652 A | 8/2000 | Matern, Jr. | |
| 6,325,069 B1 | 12/2001 | Heims | |
| D504,056 S * | 4/2005 | Craig et al. | D7/691 |
| 6,942,129 B2 * | 9/2005 | Ferraioli | 223/113 |
| 7,296,311 B1 | 11/2007 | Navarrette | |

* cited by examiner

*Primary Examiner* — Patricia Bianco
*Assistant Examiner* — Camtu Nguyen

(57) ABSTRACT

A foot stabilizing device which can be extended from between a box springs and a mattress of a user's bed to support the user's foot in an elevated position while trimming toenails or donning a sock or shoe, for example and without limitation includes a generally elongated device neck and a device platform carried by and oriented at an angle with respect to the device neck.

3 Claims, 6 Drawing Sheets

FOOT STABILIZING DEVICE

FIELD OF THE INVENTION

The disclosure generally relates to devices for supporting the feet. More particularly, the disclosure relates to a foot stabilizing device which can be extended from between a box springs and a mattress of a user's bed to support the user's foot in an elevated position while trimming toenails or donning a sock or shoe, for example and without limitation.

BACKGROUND OF THE INVENTION

Persons who suffer from ailments such as back, hip, knee problems or stiffness often encounter difficulty in performing everyday tasks such as donning shorts, socks and shoes. These actions typically require that a person raise the foot to a position which may be awkward and uncomfortable or painful. The pain or discomfort may be mitigated somewhat if the person sits on a chair, bed or the like while performing the task as the sitting position places the person's foot or lower leg into closer proximity to his or her hands. When the person is in a sitting position, however, he or she may not be able to raise his or her foot to the desired height to comfortably perform the task.

Accordingly, a foot stabilizing device which can be extended from between a box springs and a mattress of a user's bed to support the user's foot in an elevated position while trimming toenails or donning a sock or shoe, for example and without limitation, is needed.

SUMMARY OF THE INVENTION

The disclosure is generally directed to a foot stabilizing device which can be extended from between a box springs and a mattress of a user's bed to support the user's foot in an elevated position while trimming toenails or donning a sock or shoe, for example and without limitation. An illustrative embodiment of the foot stabilizing device includes a generally elongated device neck and a device platform carried by and oriented at an angle with respect to the device neck.

In some embodiments, the foot stabilizing device may include a generally elongated device neck having a device neck end; a platform attachment end opposite the device neck end; and a pair of device neck sides, a device neck upper surface and a device neck lower surface extending between the device neck end and the platform attachment end; and a device platform extending from the platform attachment end of the device neck and having a device platform bottom surface oriented at an obtuse angle with respect to the device neck lower surface of the device neck and a foot support surface opposite the device platform bottom surface.

The disclosure is further generally directed to a foot stabilizing method. An illustrative embodiment of the foot stabilizing method includes providing a foot stabilizing device having a device neck and a device platform extending from the device neck, stabilizing the device neck in a generally horizontal orientation, placing and stabilizing a user's foot on the device platform of the foot stabilizing device and having the user perform a task on the user's foot.

BRIEF DESCRIPTION OF THE DRAWINGS

The disclosure will now be made, by way of example, with reference to the accompanying drawings, in which.

DETAILED DESCRIPTION

Figure 1:
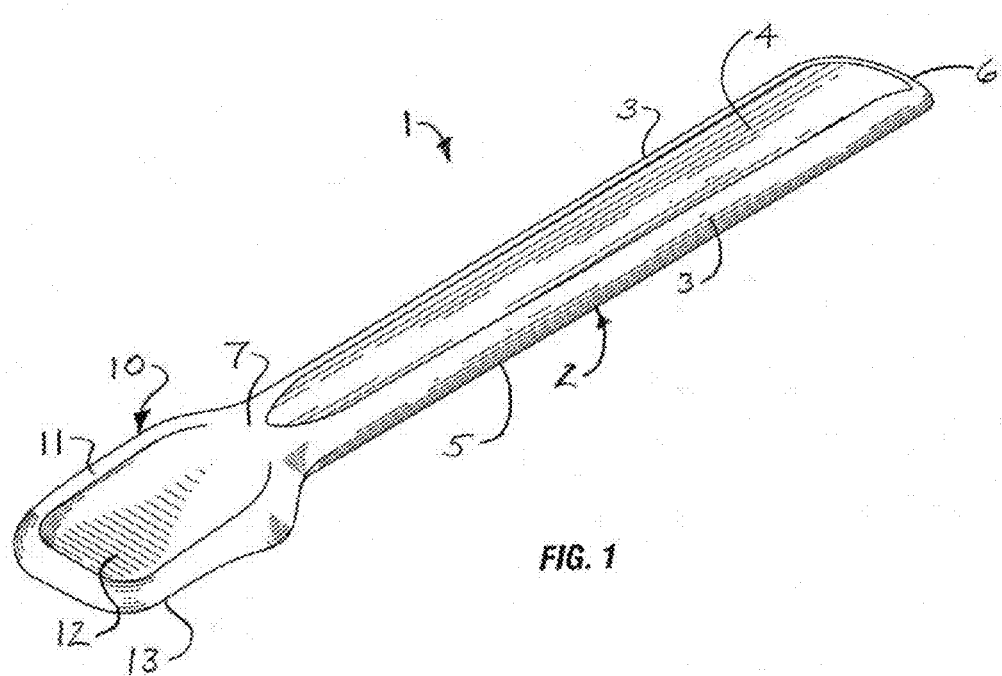
FIG. 1 is a top perspective view of an illustrative embodiment of the foot stabilizing device.
Figure 2:
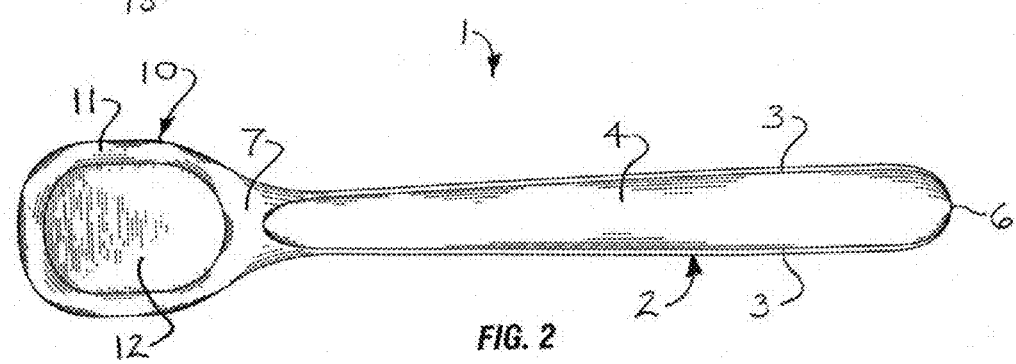
FIG. 2 is a top view of the foot stabilizing device illustrated in FIG. 1.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Referring initially to FIGS. 1-7 of the drawings, an illustrative embodiment of the foot stabilizing device, hereinafter device, is generally indicated by reference numeral 1. The device 1 may be wood, plastic, metal or any other substantially rigid material. The device 1 may include a generally elongated device neck 2 having a pair of spaced-apart device neck sides 3, a device neck upper surface 4, a device neck lower surface 5 and a device neck end 6 which may be generally curved. A device platform 10 may extend from the device neck 2 at a platform attachment end 7 which is opposite the device neck end 6. In some embodiments, the device neck 2 may be generally shaped in the configuration of a shoehorn. Accordingly, the device neck sides 3 may gradually widen or diverge from the platform attachment end 7 to the device neck end 6 of the device neck 2. The device neck upper surface 4 may be generally concave. In some applications, the device neck 2 may assist a user (not illustrated) in donning a shoe (not illustrated) in the same manner as a conventional shoehorn.

Figure 3:
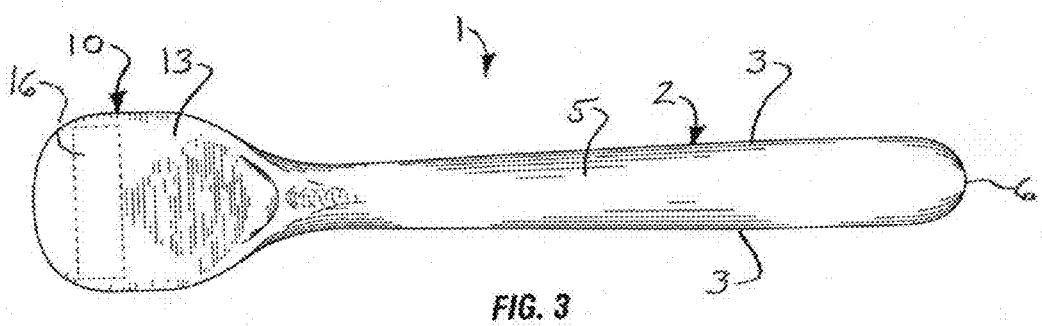
FIG. 3 is a bottom view of the foot stabilizing device.
Figure 4:
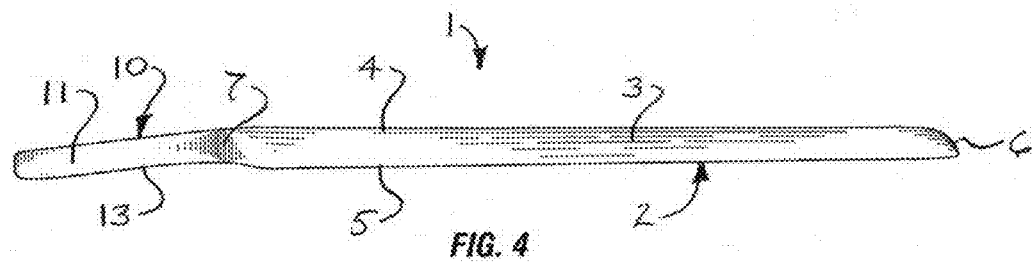
FIG. 4 is a right side view of the foot stabilizing device.
Figure 5:
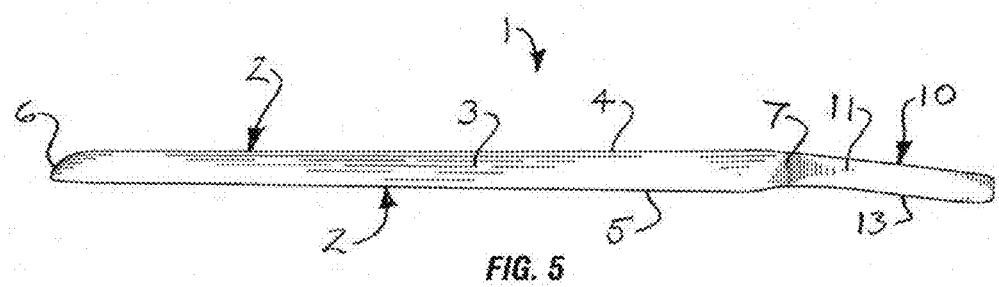
FIG. 5 is a left side view of the foot stabilizing device.
Figure 6:
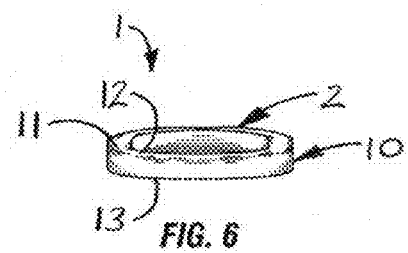
FIG. 6 is a platform end view of the foot stabilizing device.
Figure 7:
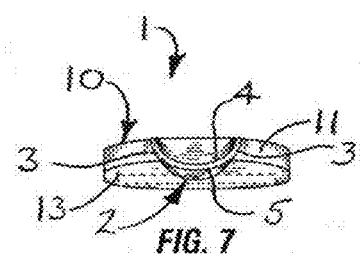
FIG. 7 is a neck end view of the foot stabilizing device.

The device platform 10 may extend from the device neck 2 at the platform attachment end 7. The device platform 10 may have a generally elongated, rectangular shape with a concave foot support surface 12 and a device platform bottom surface 13 which may be generally convex. A device platform rim 11 may surround the foot support surface 12. Accordingly, the concave foot support surface 12 with the device platform rim 11 may have a generally cup-shaped configuration which is adapted to support and stabilize the foot 25 of a user 24 (FIG. 8) as the user 24 dons a sock 26 or the like on the foot 25, as will be hereinafter described. As illustrated in FIGS. 4 and 5, in some embodiments the platform bottom surface 13 of the device platform 10 may be oriented at an obtuse or slight downward angle with respect to the device neck lower surface 5 of the device neck 2. As illustrated in FIG. 3, in some embodiments a non-slip tab 16 may be provided on the device platform bottom surface 13 of the device platform 10 to prevent the device 1 from inadvertently slipping when placed on a surface (not illustrated) during use.

Figure 8:
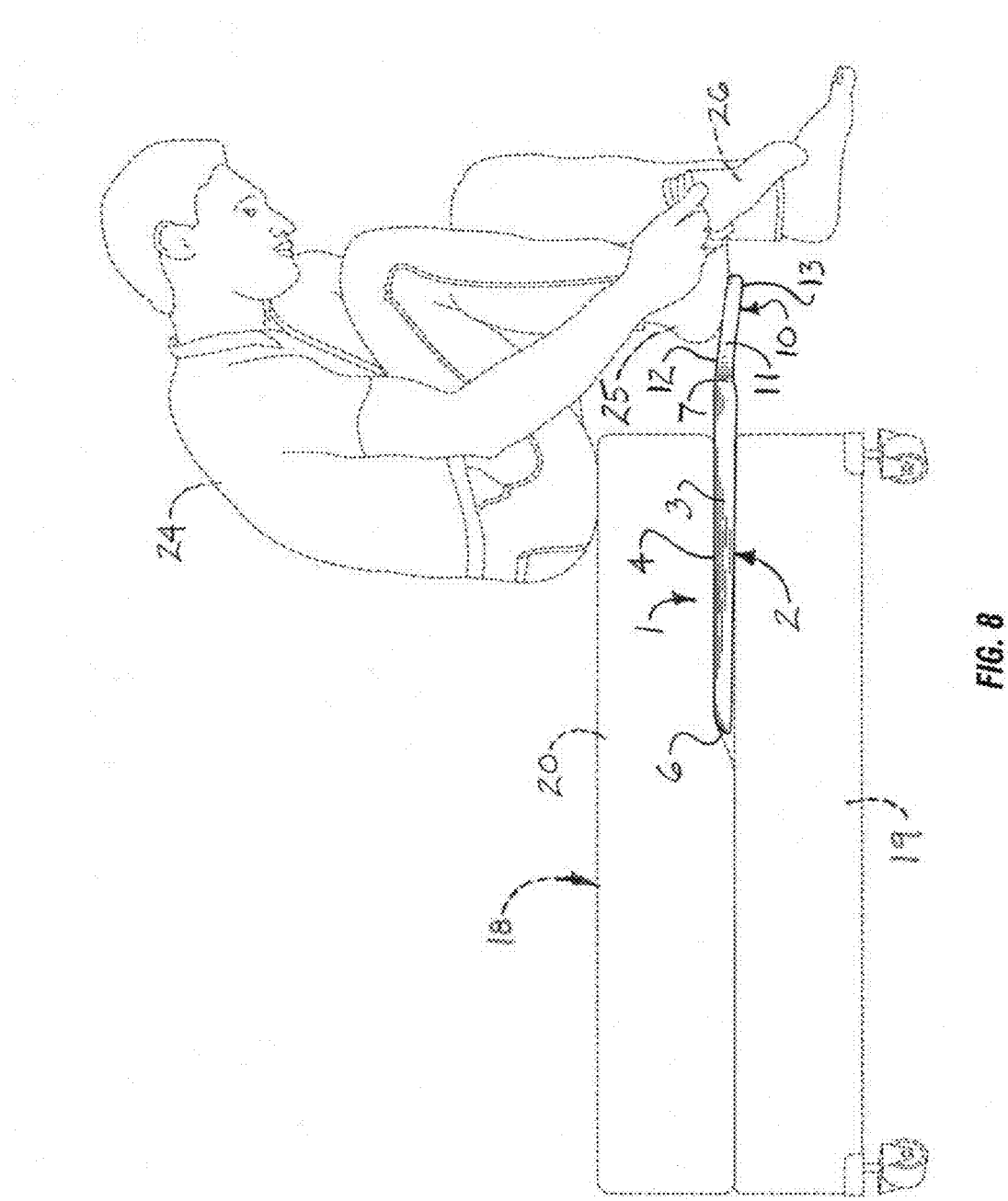
FIG. 8 is a side view of the foot stabilizing device, with the neck of the device inserted between a box springs and mattress of a bed (illustrated in phantom) and the foot of a user (illustrated in phantom) resting on the platform device as the user dons a sock on the foot.

Referring next to FIG. 8, in exemplary application the device 1 can be used to assist a user 24 in donning a sock 26 on the user's foot 25. Accordingly, the device neck 2 is initially inserted between a box springs 19 and a mattress 20 of a bed 18. The device platform 10 and a portion of the device neck 2 may protrude from the side of the bed 18. A user 24 sits on the mattress 20 of the bed 18 and places the foot 25 on which the sock 26 is to be donned on the foot support surface 12 of the device platform 10. The device platform 10 supports and stabilizes the user's foot 25 in an elevated position which facilitates ease in placing the sock 26 on the foot 25. After use, the device neck 2 may be removed from between the box springs 19 and the mattress 20. Those skilled in the art will appreciate that other furniture such as a couch or overstuffed chair could be used in place of bed 18. For example, neck 2 can be inserted between a cushion (instead of mattress 20) and frame (instead of box springs 19) of an overstuffed chair or couch to operate the claimed invention.

It will be appreciated by those skilled in the art that the device 1 can be used in any of a variety of applications in which it is necessary for the user 24 to maintain his or her foot 25 in a raised or elevated position. This includes such tasks as cutting and painting toenails, applying foot powder or spray, as well as donning socks, shoes, shorts and pants. Moreover, the device neck 3 of the device 1 may be used as a shoehorn to assist the user in donning shoes on his or her feet. Device 1 may be used upright as illustrated in FIG. 8 or it may be used upside down to utilize non-slip tab 16 to prevent the foot from slipping, for example. When not in use device 1 may be pushed between a box spring and mattress, for example, thus concealing it from view.

Figure 9:
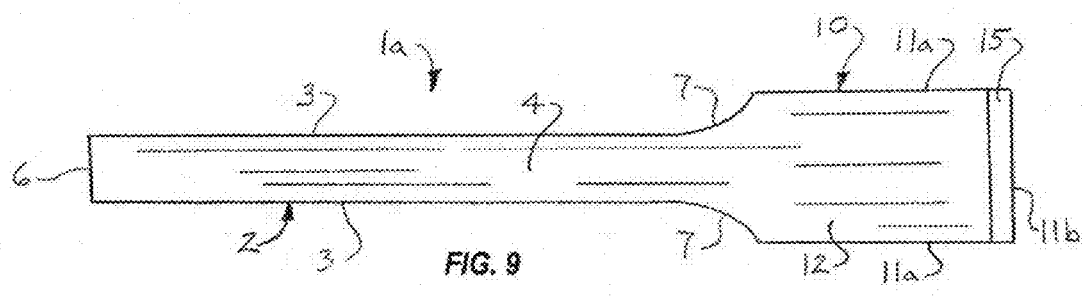
FIG. 9 is a top view of an alternative illustrative embodiment of the foot stabilizing device.
Figure 10:
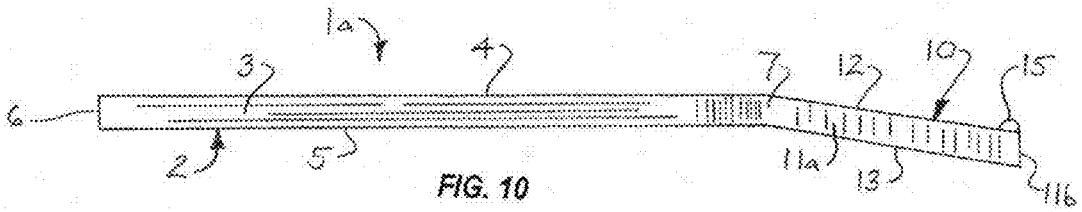
FIG. 10 is a right side view of the foot stabilizing device illustrated in FIG. 9.

Referring next to FIGS. 9 and 10 of the drawings, an alternative illustrative embodiment of the foot stabilizing device is generally indicated by reference numeral 1a. The device platform 10 of the device 1a may include pair of generally elongated, straight, parallel, spaced-apart platform sides 11a and a straight platform end 11b extending between the platform sides 11a. In some embodiments, the foot support surface 12 may be generally flat or planar. In other embodiments, the foot support surface 12 may be concave. A platform tab 15 may extend from the foot support surface 12 along the platform end 11b. As illustrated in FIG. 10, the plane of the device platform bottom surface 13 may be oriented at a downward angle with respect to the plane of the device neck lower surface 5. Application of the device 1a may be as was heretofore described with respect to the device 1 in FIG. 8.

Figure 11:
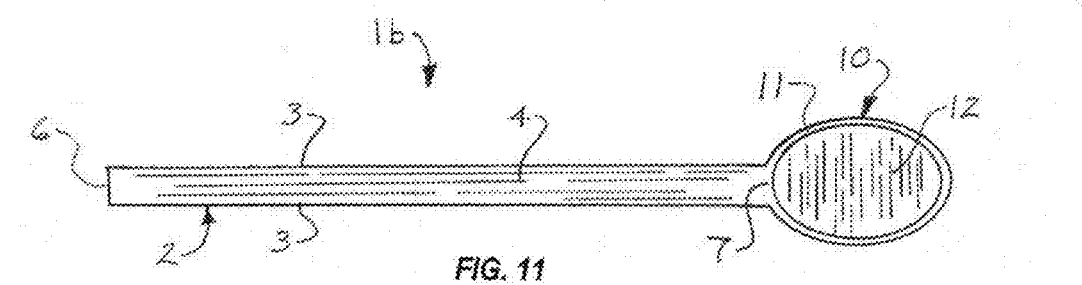
FIG. 11 is a top view of another illustrative embodiment of the foot stabilizing device.
Figure 12:
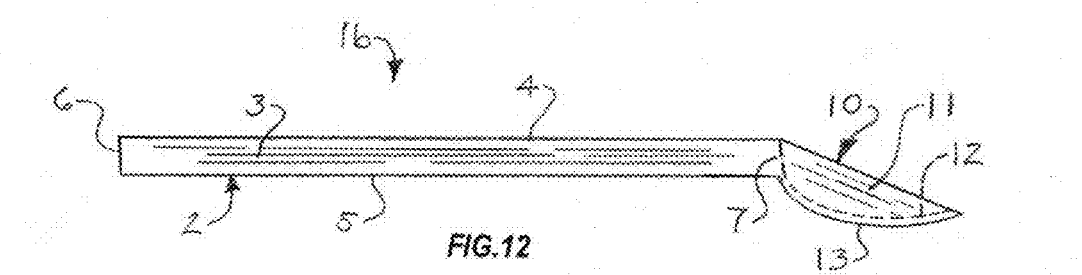
FIG. 12 is a right side view of the foot stabilizing device illustrated in FIG. 11.

Referring next to FIGS. 11 and 12 of the drawings, another illustrative embodiment of the foot stabilizing device is generally indicated by reference numeral 1b. The device platform 10 of the device 1b may include have a generally spoon shape with a concave foot support surface 12, a convex device platform bottom surface 13 and a device platform rim 11 surrounding the foot support surface 12. As illustrated in FIG. 12, the plane of the device platform 10 may be oriented at a downward angle with respect to the plane of the device neck 2. Application of the device 1b may be as was heretofore described with respect to the device 1 in FIG. 8.

Figure 13:
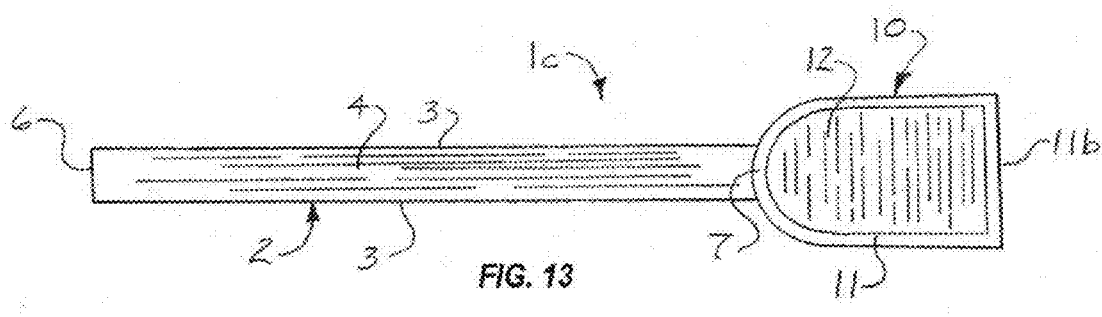
FIG. 13 is a top view of still another illustrative embodiment of the foot stabilizing device.
Figure 14:
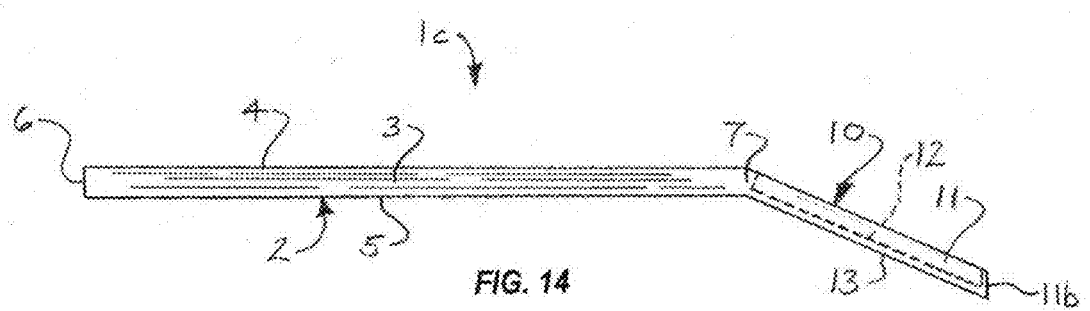
FIG. 14 is a right side view of the foot stabilizing device illustrated in FIG. 13.

Referring next to FIGS. 13 and 14 of the drawings, still another illustrative embodiment of the foot stabilizing device is generally indicated by reference numeral 1c. The device platform 10 of the device 1c may have a generally stirrup shape with a recessed, planar foot support surface 12 and a device platform rim 11 which surrounds the foot support surface 12. The device platform 10 may have a straight platform end 11b. As illustrated in FIG. 14, the plane of the device platform bottom surface 13 may be oriented at a downward angle with respect to the plane of the device neck lower surface 5. Application of the device 1c may be as was heretofore described with respect to the device 1 in FIG. 8.

Figure 15:
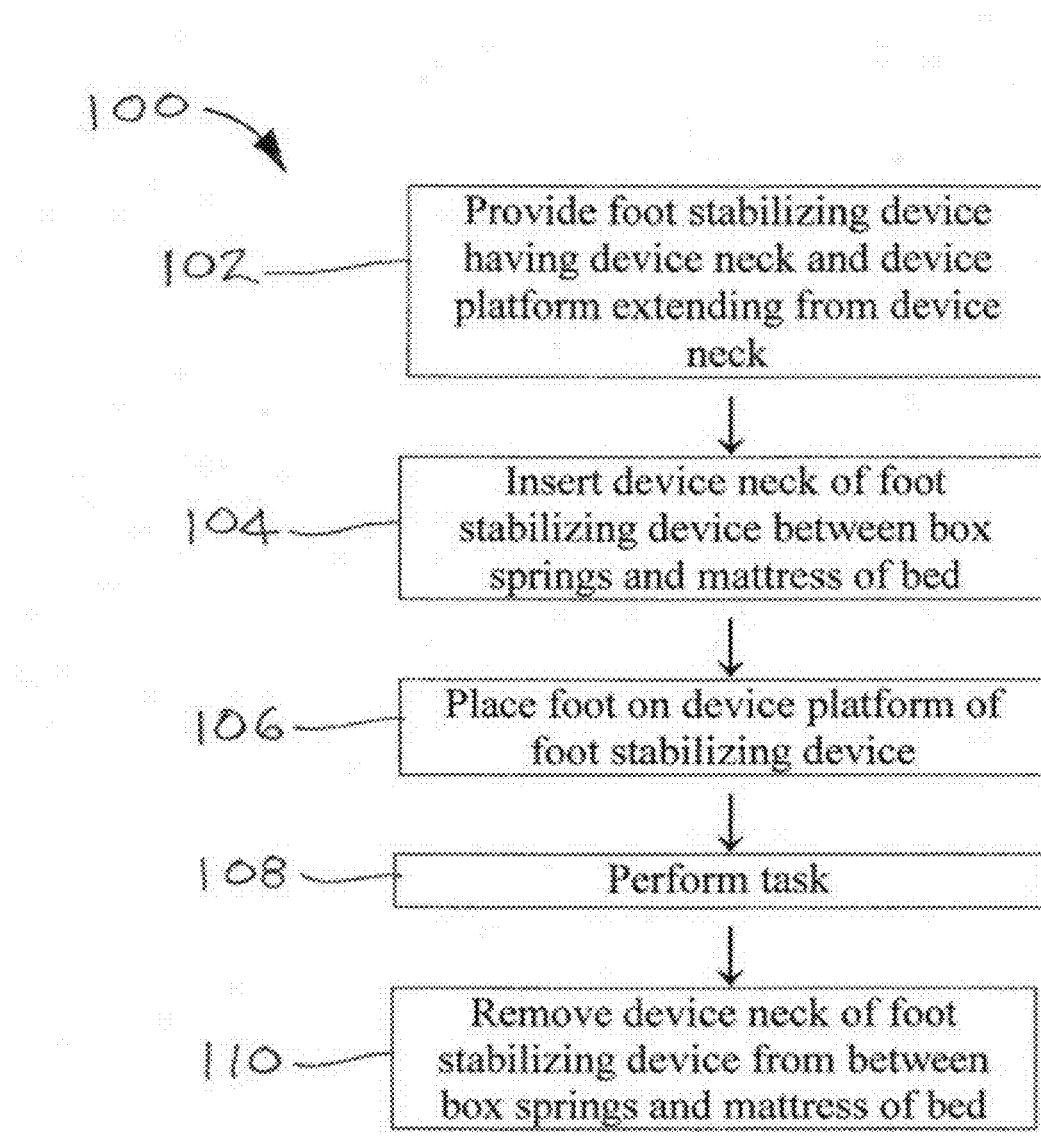
FIG. 15 is a flow diagram of an illustrative embodiment of a foot stabilizing method.

Referring next to FIG. 15 of the drawings, an illustrative embodiment of a foot stabilizing method 100 is shown. In block 102, a foot stabilizing device having a device neck and a device platform extending from the device neck is provided. In block 104, the device neck of the foot stabilizing device may be inserted between a box springs and a mattress of a bed. In block 106, a user sits on the bed and places a foot on the device platform of the foot stabilizing device. In block 108, the user performs a task. In some embodiments, the user may don a sock on the foot which is supported by the device platform. In other embodiments, the user may don a shoe on the foot which is supported by the device platform. In still other embodiments, the user may don shorts or pants or may trim toenails on the foot which is supported by the device platform. In block 110, the device neck of the foot stabilizing device may be removed from between the box springs and the mattress of the bed when the foot stabilizing device is not in use.

While various illustrative embodiments of the disclosure have been described above, it will be recognized and understood that various modifications can be made in the disclosure and the appended claims are intended to cover all such modifications which may fall within the spirit and scope of the embodiments of the disclosure.

What is claimed is:

1. A foot stabilizing method, comprising:
providing a foot stabilizing device having a device neck and a device platform extending from the device neck;
stabilizing the device neck in a generally horizontal orientation by providing a bed having box springs and a mattress on the box springs and inserting the device neck between the box springs and the mattress;
placing and stabilizing a user's foot on the device platform of the foot stabilizing device; and
having the user perform a task on the user's foot.

2. The method of claim 1 further comprising removing the device neck from between the box springs and the mattress of the bed.

3. The method of claim 1 wherein having the user perform a task on the user's foot comprises at least one of the following: donning a sock, donning a shoe, donning shorts, donning pants and trimming toenails.

* * * * *